United States Patent
Zhang et al.

(10) Patent No.: US 9,855,248 B2
(45) Date of Patent: Jan. 2, 2018

(54) POLYMORPH OF ITRACONAZOLE WITH IMPROVED PHARMACEUTICAL PROPERTIES

(71) Applicant: The Chinese University of Hong Kong, Shatin (CN)

(72) Inventors: Shuai Zhang, DaQing (CN); Hee Lum Albert Chow, Ma On Shan (CN); Wai Yip Thomas Lee, Ma On Shan (CN)

(73) Assignee: The Chinese University of Hong Kong, Shatin, N.T., Hong Kong (CN)

( * ) Notice: Subject to any disclaimer, the term of this patent is extended or adjusted under 35 U.S.C. 154(b) by 0 days.

(21) Appl. No.: 15/492,780

(22) Filed: Apr. 20, 2017

(65) Prior Publication Data
US 2017/0319553 A1    Nov. 9, 2017

Related U.S. Application Data

(60) Provisional application No. 62/333,335, filed on May 9, 2016.

(51) Int. Cl.
*C07D 405/14* (2006.01)
*A61K 31/496* (2006.01)
*A61K 31/4196* (2006.01)
*G01N 23/20* (2006.01)
*C07D 249/12* (2006.01)
*G01N 21/35* (2014.01)

(52) U.S. Cl.
CPC ........ *A61K 31/4196* (2013.01); *C07D 249/12* (2013.01); *C07D 405/14* (2013.01); *G01N 23/20* (2013.01); *G01N 2021/3595* (2013.01)

(58) Field of Classification Search
None
See application file for complete search history.

(56) References Cited

U.S. PATENT DOCUMENTS 7,446,107 B2 * 11/2008 Remenar .............. A61K 9/0014
  514/254.07
2003/0100568 A1 * 5/2003 Werling .................. A61K 9/10
  514/254.07

* cited by examiner

*Primary Examiner* — Emily A Bernhardt
(74) *Attorney, Agent, or Firm* — Kilpatrick Townsend & Stockton LLP (57) ABSTRACT

The present invention provides a new crystalline form of itraconazole as well as the method of making same.

12 Claims, 10 Drawing Sheets

POLYMORPH OF ITRACONAZOLE WITH IMPROVED PHARMACEUTICAL PROPERTIES

CROSS-REFERENCES TO RELATED APPLICATIONS

This application claims priority to U.S. Provisional Patent Application No. 62/333,335, filed May 9, 2016, the contents of which are hereby incorporated by reference in the entirety for all purposes.

BACKGROUND

Poor or limited drug solubility is one of the major challenges in oral drug delivery. It is well recognized that amorphization through molecular dispersion in a hydrophilic polymer (commonly known as amorphous solid dispersion) can increase the aqueous solubilities, dissolution rates, and possibly oral bioavailabilies of poorly water-soluble drugs. Despite the widely documented utility of this approach to resolving the solubility-related absorption issue of problematic drugs, the number of amorphous drug products that have successfully made their way to the market is still limited, which can be attributed to their inherently poor stability. Owing to their high free energy and thermodynamic activity, amorphous solids tend to revert back to their low-energy crystalline counterparts during storage, processing and/or dissolution, resulting in a complete loss of their unique advantage in solubility and bioavailability enhancement.

A review of the literature showed that most of the studies on amorphous solid dispersions focused on the characterization of drug-polymer miscibility, thermal properties, spectral characteristics, dissolution performance and physical stability under stressed conditions. Very few of these studies have attempted to elucidate the recrystallization behaviors of dispersed drugs in these systems. In addition, while the literature is replete with information on the solution-phase crystallization of drugs, very little is known about the solid-state crystallization behaviors of amorphous drugs in polymeric matrix, particularly for drugs capable of crystallizing into different polymorphs with different free energies and thermodynamic stabilities. Typically, upon recrystallization from the amorphous state, the relatively unstable polymorph will form first, as it is relatively close in free energy to the parent phase (Ostwald rule of stages). However, this unstable (metastable) polymorph will eventually revert to the stable form because of the associated favorable reduction in free energy. By elucidating the mechanisms of polymorph selectivity and establishing the conditions under which this occurs in the solid state, rational and effective strategies can be devised to control the formation of particular polymorph or to kinetically stabilize the solid drug in its amorphous form. The latter is commonly achieved by dispersing the drug in hydrophilic polymers as amorphous solid dispersions. Polymers can be selected based on their ability to inhibit the crystallization of the initially formed (unstable) polymorph, and the best polymer would be the one that exhibits the strongest crystal growth inhibition and offers the drug maximum physical stability.

Aimed at acquiring a mechanistic understanding of the crystallization behaviors and polymorph selectivity of amorphous drugs, the present study has employed itraconazole (ITZ) as a model compound. ITZ, a synthetic triazole antifungal agent, is a BCS II compound with extremely low water-solubility (1 ng/ml at pH 7.4), which may account for the relatively low oral bioavailability (~55%) of its commercial product, Sporanox®. Moreover, ITZ has a relatively high glass transition temperature ($T_g \approx 59°$ C.) and tends to form a fairly stable amorphous form through various processing treatments such as melt-quenching and lyophilization. Thus far, only one polymorph (Form I) has been reported in the literature. U.S. Application Publication No. 2003/0100568 documents the existence of a second polymorph (Form II). Although the physical stability of amorphous ITZ formulations has been extensively studied, none of these studies has delved into the polymorphic crystallization mechanism of pure amorphous ITZ, which may be important for successful development of stable ITZ solid dispersion systems.

BRIEF SUMMARY OF THE INVENTION

In one embodiment, the present invention provides a crystalline form of itraconazole characterized by an X-ray powder diffraction (XRPD) pattern comprising three or more peaks at 11.9, 16.7, 17.4, 18.7, 19.1, 20.0 and 21.1 degrees 2θ (±0.2 degrees 2θ), wherein the XRPD is made using CuK$_{\alpha 1}$ radiation.

In a second embodiment, the present invention provides a method of preparing a crystalline Form III of itraconazole, comprising heating solid amorphous itraconazole at a temperature of from about 30° C. to about 100° C., thereby preparing crystalline Form III of itraconazole.

In a third embodiment, the present invention provides a pharmaceutical composition comprising a therapeutically effective amount of a crystalline form of itraconazole of the present invention, and a pharmaceutically acceptable carrier or excipient.

BRIEF DESCRIPTION OF THE DRAWINGS

FIG. 1A-H shows Morphologies of ITZ crystals grown under different conditions.

FIG. 2A-F shows PXRD patterns of various ITZ polymorphs. Samples recrystallized from melts were scraped from glass coverslips for the PXRD analysis.

FIG. 3A-F shows hot-stage microscopic examination of ITZ polymorphs at different temperatures.

FIG. 5 shows FTIR spectra of ITZ polymorphs. Arrows indicate the characteristic peaks (1699 cm$^{-1}$, 1010 cm$^{-1}$, 998 cm$^{-1}$, 899 cm$^{-1}$ for Form I; 1705 cm$^{-1}$, 1692 cm$^{-1}$, 1013 cm$^{-1}$ for Form II; 1696 cm$^{-1}$, 1010 cm$^{-1}$ for Form III) used to identify the polymorphs.

DETAILED DESCRIPTION OF THE INVENTION

I. General

The compound itraconazole, (2R,4S)-rel-1-(Butan-2-yl)-4-{4-[4-(4-{[(2R,4S)-2-(2,4-dichlorophenyl)-2-(1H-1,2,4-triazol-1-ylmethyl)-1,3-dioxolan-4-yl]methoxy}phenyl)piperazin-1-yl]phenyl}-4,5-dihydro-1H-1,2,4-triazol-5-one, Compound I, is an antifungal agent:

Compound I

The present invention results from the surprising discoveries a new solid Form III of Compound I, advantages attributed to the form described herein, and a melt process for making the solid Form III.

II. Definitions

As used in the present specification, the following words and phrases are generally intended to have the meanings as set forth below, except to the extent that the context in which they are used indicates otherwise.

"Therapeutically effective amount" refers to an amount that is sufficient to effect treatment, as defined below, when administered to a mammal in need of such treatment. The therapeutically effective amount will vary depending upon the subject being treated, the weight and age of the subject, the severity of the disease condition, the manner of administration and the like, which can readily be determined by one of ordinary skill in the art.

"Substantially free of other crystalline forms of Compound I" refers to a crystalline form of Compound I that contains less than 10% of other crystalline forms of Compound I, such as Form I and Form II. For example, substantially free can refer to a crystalline form of Compound I that contains less than 9, 8, 7, 6, 5, 4, 3, 2, or 1% of other crystalline forms of Compound I. Preferably, substantially free refers to a crystalline form of Compound I that contains less than 5% of other crystalline forms of Compound I. Preferably, substantially free refers to a crystalline form of Compound I that contains less than 1% of other crystalline forms of Compound I.

III. Solid Form III of Compound I

The present invention provides solid Form III of itraconazole, (2R,4S)-rel-1-(Butan-2-yl)-4-{4-[4-(4-{[(2R,4S)-2-(2,4-dichlorophenyl)-2-(1H-1,2,4-triazol-1-ylmethyl)-1,3-dioxolan-4-yl]methoxy}phenyl)piperazin-1-yl]phenyl}-4,5-dihydro-H-1,2,4-triazol-5-one, Compound I, including crystalline and amorphous forms, as well as solvate and hydrate forms. In some embodiments, the present invention provides a crystalline form of Compound I having the structure:

Compound I and solvates or hydrates thereof.

Compound I can adopt a variety of solid forms, including, but not limited to, Form I, Form II, and Form III. Compound I can form a mixture of two or more crystalline forms, or form a single crystalline form substantially free of other crystalline forms.

Figure 1A:
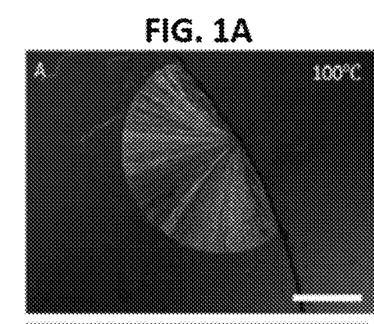
(FIG. 1A) Form I crystal grew by diffusion from the side of the bulk at 100° C., (FIG. 1B) Bulk Form II crystals at 100° C.
Figure 1B:
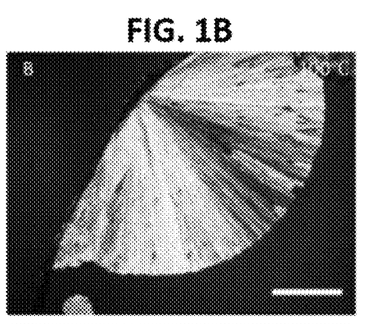
Figure 1C:
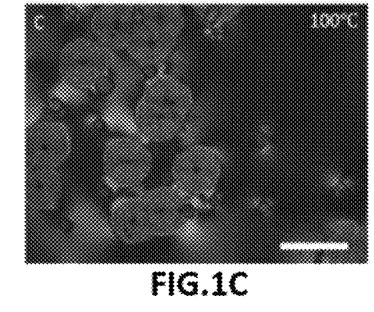
(FIG. 1C) Bulk Form III crystals at 100° C.
Figure 1D:
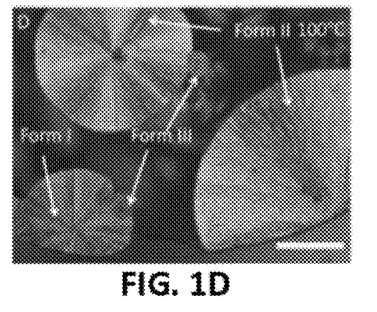
(FIG. 1D) Bulk Form I, II and III crystals at 100° C.; arrows indicate respective polymorphs.
Figure 1E:
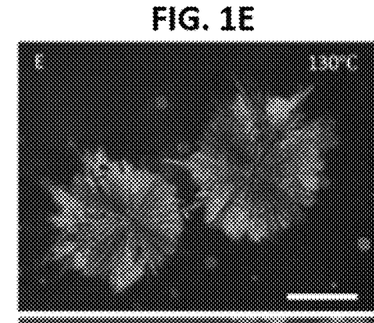
(FIG. 1E) Bulk Form I crystals grown at 130° C.
Figure 1F:
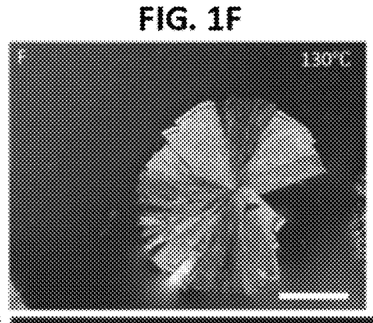
(FIG. 1F) Bulk Form II crystals grown at 130° C.
Figure 1G:
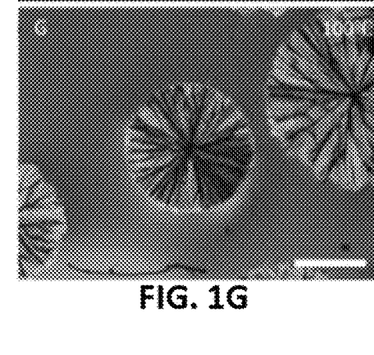
(FIG. 1G) Surface Form I crystals at 100° C.
Figure 1H:
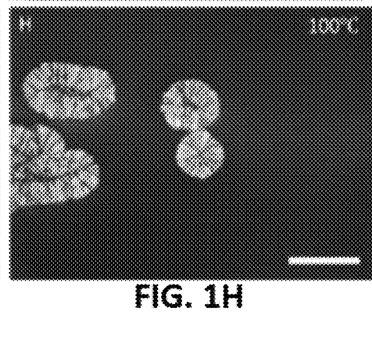
(FIG. 1H) Surface Form II crystals at 100° C. Scale bar equals 1000 μm.
Figure 2A:
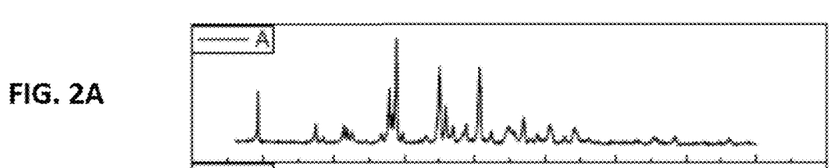
(FIG. 2A) Form I.

Crystalline Form I of Compound I is also known and is characterized by an X-ray powder diffraction pattern having peaks at 14.9, 17.6, 20.5, 23.6, 25.4, and 27.2 degrees 2θ (±0.2 degrees 2θ), wherein the XRPD is made using CuK$_{α1}$ radiation. The XRPD of crystalline Form I of Compound I is also shown in FIG. 2A. Crystalline Form I of Compound I is also characterized by a Fourier Transform Infrared (FTIR) spectrum comprising peaks at 899, 998, 1010 and 1699 cm$^{-1}$.

Figure 2B:
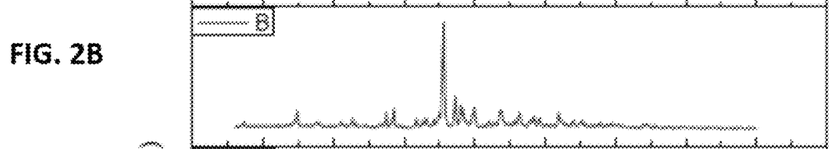
(FIG. 2B) Form II.

Crystalline Form II of Compound I is also known and is characterized by an X-ray powder diffraction pattern having peaks at 7.3, 19.9, 21.9, 26.1 and 32.2 degrees 2θ (±0.2 degrees 2θ), wherein the XRPD is made using CuK$_{α1}$ radiation. The XRPD of crystalline Form II of Compound I is also shown in FIG. 2B. Crystalline Form II of Compound I is also characterized by a Fourier Transform Infrared (FTIR) spectrum comprising peaks at 1013, 1692 and 1705 cm$^{-1}$.

Crystalline Form III of Compound I can be characterized by an X-ray powder diffraction (XRPD) pattern having at least three, four, five, or more, peaks at 11.9, 16.7, 17.4, 18.7, 19.1, 20.0 or 21.1 degrees 2θ (±0.2 degrees 2θ), wherein the XRPD is made using CuK$_{α1}$ radiation. In some embodiments, the crystalline Form III of Compound I can be characterized by an X-ray powder diffraction pattern having at least three peaks at 11.9, 16.7, 17.4, 18.7, 19.1, 20.0 or 21.1 degrees 2θ (±0.2 degrees 2θ), wherein the XRPD is made using CuK$_{α1}$ radiation. In some embodiments, the crystalline Form III of Compound I can be characterized by an X-ray powder diffraction pattern having at least four peaks at 11.9, 16.7, 17.4, 18.7, 19.1, 20.0 or 21.1 degrees 2θ (±0.2 degrees 2θ), wherein the XRPD is made using CuK$_{α1}$ radiation. In some embodiments, the crystalline Form III of Compound I can be characterized by an XRPD pattern having at least five peaks at 11.9, 16.7, 17.4, 18.7, 19.1, 20.0 or 21.1 degrees 2θ (±0.2 degrees 2θ), wherein the XRPD is made using CuK$_{α1}$ radiation. In some embodiments, the crystalline Form III of Compound I can be characterized by an XRPD pattern having peaks at 11.9, 16.7, 17.4, 18.7, 19.1, 20.0 and 21.1 degrees 2θ (±0.2 degrees 2θ), wherein the XRPD is made using CuK$_{α1}$ radiation. In some embodiments, the crystalline Form III of Compound I can be characterized by the XRPD pattern substantially in accordance with that of FIG. 2C.

Form III of Compound I can also be characterized by a Fourier Transform Infrared (FTIR) spectrum comprising peaks at 1010 and 1696 cm$^{-1}$. In some embodiments, the crystalline Form III of Compound I can be characterized by an FTIR spectrum having peaks at 1010 and 1696 cm$^{-1}$. In some embodiments, the crystalline Form III of Compound I can be characterized by an FTIR spectrum having a peak at 1696 cm$^{-1}$.

Form III of Compound I can also be characterized by a melting point temperature of 119° C. In some embodiments, the crystalline Form III of Compound I can be characterized by a melting point temperature of 119° C.

In some embodiments, the crystalline Form III of Compound I can be characterized by an XRPD pattern having peaks at 11.9, 16.7, 17.4, 18.7, 19.1, 20.0 and 21.1 degrees 2θ (±0.2 degrees 2θ), wherein the XRPD is made using CuK$_{α1}$ radiation, and an FTIR spectrum having a peak at 1696 cm$^{-1}$. In some embodiments, the crystalline Form III of Compound I can be characterized by an XRPD pattern having peaks at 11.9, 16.7, 17.4, 18.7, 19.1, 20.0 and 21.1 degrees 2θ (±0.2 degrees 2θ), wherein the XRPD is made using CuK$_1$ radiation, an FTIR spectrum having a peak at 1696 cm$^{-1}$, and a melting point temperature of 119° C.

In some embodiments, the crystalline Form III of Compound I can be substantially free of other crystalline forms of Compound I. In some embodiments, the crystalline Form III of Compound I can be substantially free of crystalline Form I and Form II of Compound I. In some embodiments, the crystalline Form III of Compound I can be substantially free of crystalline Form I of Compound I, characterized by the XRPD pattern substantially in accordance with that of FIG. 2A. In some embodiments, the crystalline Form III of Compound I can be substantially free of crystalline Form II of Compound I, characterized by the XRPD pattern substantially in accordance with that of FIG. 2B.

Any formula or structure given herein, including Compound I, is also intended to represent unlabeled forms as well as isotopically labeled forms of the compounds. Isotopically labeled compounds have structures depicted by the Formulae given herein except that one or more atoms are replaced by an atom having a selected atomic mass or mass number. Examples of isotopes that can be incorporated into compounds of the disclosure include isotopes of hydrogen, carbon, nitrogen, oxygen, phosphorous, fluorine and chlorine, such as, but not limited to 2H (deuterium, D), $^3$H (tritium), $^{11}$C, $^{13}$C, $^{14}$C, $^{15}$N, $^{18}$F, $^{31}$P, $^{32}$P, $^{35}$S, $^{36}$Cl and $^{125}$I. Various isotopically labeled compounds of the present disclosure, for example those into which radioactive isotopes such as $^3$H, $^{13}$C and $^{14}$C are incorporated. Such isotopically labeled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients.

The disclosure also includes Compound I in which from 1 to "n" hydrogens attached to a carbon atom is/are replaced by deuterium, in which n is the number of hydrogens in the molecule. Such compounds exhibit increased resistance to metabolism and are thus useful for increasing the half-life of any Compound I when administered to a mammal. See, for example, Foster, "Deuterium Isotope Effects in Studies of Drug Metabolism", *Trends Pharmacol. Sci.* 5(12):524-527 (1984). Such compounds are synthesized by means well known in the art, for example by employing starting materials in which one or more hydrogen atoms have been replaced by deuterium.

Deuterium labeled or substituted therapeutic compounds of the disclosure may have improved DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life or reduced dosage requirements. An $^{18}$F labeled compound may be useful for PET or SPECT studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. Further, substitution with heavier isotopes, particularly deuterium (i.e., $^2$H or D) may afford certain therapeutic advantages resulting from greater metabolic stability, for example increased in vivo half-life or reduced dosage requirements or an improvement in therapeutic index. It is understood that deuterium in this context is regarded as a substituent in Compound I.

The concentration of such a heavier isotope, specifically deuterium, may be defined by an isotopic enrichment factor.

In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this disclosure any atom specifically designated as a deuterium (D) is meant to represent deuterium.

IV. Methods of Preparing Solid Forms of Compound I

The solid forms of Compound I can be prepared by a variety of methods. For example, Compound I can be dissolved in a single solvent system and allowed to crystallize. Alternatively, Compound I can be crystallized from a two-solvent system by dissolving Compound I in a solvent, and then adding an anti-solvent to the mixture causing Compound I to crystallize.

Alternatively, crystalline compounds can be prepared by heating a solid amorphous form of the compound at a temperature below the melting point temperature until the crystalline form of the compound is formed. This can be performed at a single temperature, or multiple temperatures. For example, the solid amorphous compound can be heated at a first temperature for a first interval of time, and then heated at a second temperature for a second interval of time, where the first temperature can be at about the glass transition temperature of the compound and the second temperature can be above the glass transition temperature and below the melting point temperature of the crystalline form of the compound. For example, heating solid amorphous Compound I to a temperature of from about 30° C. to about 100° C. can prepare crystalline Form III of Compound I. The glass transition temperature of Compound I is about 59° C. and the melting point temperature of crystalline Form III of Compound I is about 119° C. In some embodiments, the present invention provides a method of preparing a crystalline Form III of itraconazole, comprising heating the solid amorphous itraconazole at a temperature of about the glass transition temperature of itraconazole, and heating the solid amorphous itraconazole at a second temperature above the glass transition temperature and below the melting temperature of itraconazole. In some embodiments, the present invention provides a method of preparing a crystalline Form III of itraconazole, comprising heating the solid amorphous itraconazole at a temperature of from about 50 to about 60° C., and heating the solid amorphous itraconazole at a second temperature of about 100° C.

The methods of preparing crystalline forms of Compound I can be performed under any suitable reaction conditions. For example, the methods of preparing the crystalline forms of Compound I can be performed at any suitable temperature, such as, but not limited to, below room temperature, at room temperature, or above room temperature. In some embodiments, the temperature can be from about −78° C. to about 100° C., or from about 0° C. to about 50° C., or from about 10° C. to about 30° C. In some embodiments, the temperature can be the reflux temperature of the particular solvent used in the method. In other embodiments, crystalline forms of Compound I can be heated above about 100° C. such that one crystalline form of Compound I forms a second crystalline form of Compound I.

The methods of preparing crystalline forms of Compound I can be performed for any suitable time. For example, the time can be for minutes, hours or days. Representative times for preparing the crystalline Form III of Compound I include 1, 2, 3, 4, 5, 6, 7, 8, 9, 10, 11, 12, 16, 20 or 24 hours. In some embodiments, the crystalline Form III of Compound I can be prepared by heating amorphous Compound I to a temperature of from about 30° C. to about 100° C. for about 10 hours. In some embodiments, the present invention provides a method of preparing a crystalline Form III of itraconazole, comprising heating solid amorphous itraconazole at a temperature of from about 30° C. to about 100° C., thereby preparing crystalline Form III of itraconazole. In some embodiments, the method comprises heating the solid amorphous itraconazole at a first temperature of from about 50° C. to about 60° C., and heating the solid amorphous itraconazole at a second temperature of about 100° C.

Any suitable interval of time can be used in the method of the present invention. For example, the heating can be for minutes, hours or days. Representative intervals include, but are not limited to, 1 hour, or 2, 4, 6, 8, 10, 12, 16, 20, or 24 hours. Other representative intervals include, but are not limited to, 1 day, or 2, 3, 4, 5, 6 or 7 days. In some embodiments, the method comprises heating the solid amorphous itraconazole at a first temperature of from about 50° C. to about 60° C. for a first period of at least 1 day, and heating the solid amorphous itraconazole at a second temperature of about 100° C. In some embodiments, the method comprises heating the solid amorphous itraconazole at a first temperature of from about 50° C. to about 60° C. for a first period of 4 to 5 days, and heating the solid amorphous itraconazole at a second temperature of about 100° C.

The methods of preparing crystalline forms of Compound I can be also be performed at any suitable pressure. For example, the pressure can be below atmospheric pressure, at about atmospheric pressure, or above atmospheric pressure.

Crystallization can be induced by methods known in the art, for example by mechanical means such as scratching or rubbing the contact surface of the reaction vessel with e.g. a glass rod. Optionally the saturated or supersaturated solution may be inoculated with seed crystals. The mixture for crystallizing Compound I can also contain a seed crystal of crystalline Compound I.

Isolation of the desired crystalline form can be accomplished by removing the solvent and precipitating solvent from the crystals. Generally this is carried out by known methods, such as, filtration, suction filtration, decantation or centrifugation. Further isolation can be achieved by removing any excess of the solvent(s) from the crystalline form by methods known to the one skilled in the art as for example application of a vacuum, and/or by heating.

V. Pharmaceutical Compositions

The solid forms of Compound I provided herein can be administered in the form of pharmaceutical compositions. This disclosure provides pharmaceutical compositions that contain, as the active ingredient, one or more of the solid forms of Compound I described or a pharmaceutically acceptable salt or ester thereof and one or more pharmaceutically acceptable excipients, carriers, including inert solid diluents and fillers, diluents, including sterile aqueous solution and various organic solvents, permeation enhancers, solubilizers and adjuvants. The pharmaceutical compositions may be administered alone or in combination with other therapeutic agents (as indicated in the Combination Therapy section below). Such compositions are prepared in a manner well known in the pharmaceutical art (see, e.g., Remington's Pharmaceutical Sciences, Mace Publishing Co., Philadelphia, Pa. 17th Ed. (1985); and Modern Pharmaceutics, Marcel Dekker, Inc. 3rd Ed. (G. S. Banker & C. T. Rhodes, Eds.)

The pharmaceutical compositions may be administered in either single or multiple doses by any of the accepted modes of administration of agents having similar utilities, for example as described in those patents and patent applications incorporated by reference, including rectal, buccal, intranasal and transdermal routes, by intra-arterial injection, intravenously, intraperitoneally, parenterally, intramuscularly, subcutaneously orally, topically, as an inhalant or via an impregnated or coated device such as a stent, for example or an artery-inserted cylindrical polymer.

One mode for administration is parenteral, particularly by injection. The forms in which the novel compositions of the present disclosure may be incorporated for administration by injection include aqueous or oil suspensions or emulsions, with sesame oil, corn oil, cottonseed oil or peanut oil, as well as elixirs, mannitol, dextrose or a sterile aqueous solution and similar pharmaceutical vehicles. Aqueous solutions in saline are also conventionally used for injection, but less preferred in the context of the present disclosure. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating a compound according to the present disclosure in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the general methods of preparation are vacuum-drying and freeze-drying techniques which yield a powder of the active ingredient plus any additional desired ingredient from a previously sterile-filtered solution thereof.

Oral administration is another route for administration of compounds in accordance with the disclosure. Administration may be via capsule or enteric coated tablets or the like. In making the pharmaceutical compositions that include at least one compound described herein, the active ingredient is usually diluted by an excipient and/or enclosed within such a carrier that can be in the form of a capsule, sachet, paper or other container. When the excipient serves as a diluent, it can be in the form of a solid, semi-solid or liquid material (as above), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup and methyl cellulose. The formulations can additionally include: lubricating agents such as talc, magnesium stearate and mineral oil; wetting agents; emulsifying and suspending agents; preserving agents such as methyl and propylhydroxy-benzoates; sweetening agents; and flavoring agents.

The compositions of the disclosure can be formulated so as to provide quick, sustained or delayed release of the active ingredient after administration to the patient by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345. Another formulation for use in the methods of the present disclosure employs transdermal delivery devices ("patches"). Such transdermal patches may be used to provide continuous or discontinuous infusion of the compounds of the present disclosure in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile or on demand delivery of pharmaceutical agents.

In some embodiments, the compositions are formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient (e.g., a tablet, capsule, ampoule). The compounds are generally administered in a pharmaceutically effective amount. In some embodiments, each dosage unit contains from 1 mg to 2 g of a compound described herein and for parenteral administration, in some embodiments, from 0.1 to 700 mg of a compound a compound described herein. It will be understood, however, that the amount of the compound actually administered usually will be determined by a physician, in the light of the relevant circumstances, including the condition to be treated, the chosen route of administration, the actual compound administered and its relative activity, the age, weight and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present disclosure. When referring to these preformulation compositions as homogeneous, it is meant that the active ingredient is dispersed evenly throughout the composition so that the composition may be readily subdivided into equally effective unit dosage forms such as tablets, pills and capsules.

The tablets or pills of the present disclosure may be coated or otherwise compounded to provide a dosage form affording the advantage of prolonged action or to protect from the acid conditions of the stomach. For example, the tablet or pill can comprise an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

Compositions for inhalation or insufflation include solutions and suspensions in pharmaceutically acceptable, aqueous or organic solvents or mixtures thereof and powders. The liquid or solid compositions may contain suitable pharmaceutically acceptable excipients as described supra. In some embodiments, the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a facemask tent or intermittent positive pressure breathing machine. Solution, suspension or powder compositions may be administered, in some embodiments orally or nasally, from devices that deliver the formulation in an appropriate manner.

In one embodiment, this disclosure relates to a pharmaceutical composition comprising a pharmaceutically acceptable excipient or carrier and a therapeutically effective amount of the compound of Compound I as described above or a pharmaceutically acceptable salt, ester, prodrug, stereoisomer or hydrate thereof. In some embodiments, the present invention provides a pharmaceutical composition comprising a therapeutically effective amount of a crystalline form of itraconazole of the present invention, and a pharmaceutically acceptable carrier or excipient.

VI. Examples

Chemicals and Reagents

Itraconazole: ((2R,4S)-rel-1-(butan-2-yl)-4-{4-[4-(4-{[(2R,4S)-2-(2,4-dichlorophenyl)-2-(1H-1,2,4-triazol-1-ylmethyl)-1,3-dioxolan-4-yl]methoxy phenyl)piperazin-1yl] phenyl}-4,5-dihydro-1H-1,2,4-triazol-5-one, ITZ, Form I) with a purity>99.0% was purchased from YICK-VIC (Hong Kong). Ethanol, acetonitrile, and formic acids were of analytical grade (with >99% purity) and purchased from VWR Chemical Co. Ltd. (Hong Kong).

Preparation of Amorphous ITZ

About 4-5 mg of crystalline ITZ was melted at 175° C. between two glass coverslips in a temperature-controlled oven and the sample was then rapidly quenched to room temperature to form an amorphous solid. The solidified sample was confirmed to be crystal-free by means of a polarized light microscope (Axioplan 2 imaging and Axiophot 2 microscope, Carl Zeiss Corp, Hong Kong). For the bulk recrystallization studies, samples were stored at different elevated temperatures to initiate recrystallization while for the surface recrystallization experiments, one of the coverslips was carefully removed to expose a free surface before storing the samples. Crystal morphology was examined using the polarized light microscope as before.

Differential Scanning Calorimetry (DSC)

Thermal analysis was conducted using a Perkin Elmer Q6000 differential scanning calorimeter. Different forms of ITZ were allowed to recrystallize between two glass coverslips. Once recrystallization was completed, the top coverslip was gently removed and the materials in different growth zones were carefully scraped off from the surface of the bottom coverslip. Accurately weighed quantity (2-3 mg) of each ITZ polymorph was encapsulated in a hermetically sealed aluminum pan, and scanned from 30° C. to 180° C. at 3° C./min under $N_2$ purge at 50 ml/min. The enthalpies of fusion ($\Delta H^f$) of the different forms were determined and the corresponding entropies of fusion ($\Delta S^f$) were calculated from the relation, $\Delta S^f = \Delta H^f/T_m$, where $T_m$ is the melting point. In addition, the thermal behaviors of Form III were investigated at different heating rates.

X-Ray Powder Diffraction (XRPD)

X-ray powder diffraction (XRPD) data were collected using a powder X-ray diffractometer (Philips, Xpert PRO, The Netherlands) equipped with a Cu radiation source operating at 40 kV and 40 mV. Sample was uniformly packed into a custom-made aluminum holder with a 2 mm depth and scanned from 2θ of 3° to 40θ at a rate of 4°/min with a step size of 0.017°.

Fourier Transform Infrared (FTIR) Spectroscopy

FTIR measurement was conducted using a Bruker Alpha FTIR (Bruker, Hong Kong) in the wavenumber range of 4000 cm$^{-1}$ to 400 cm$^{-1}$ in the transmittance mode. One hundred and twenty-eight scans were collected at a resolution of 4 cm$^{-1}$ for each sample.

Example 1. Preparation of Form III of Compound I

Amorphous itraconazole was recrystallized from melt between two glass coverslips by heating the coverslips at a temperature of less than 100° C. Itraconazole is first heated to 180° C. (around 10° C. higher than the melting point of Form I) between two cover glasses until melting is completed, and then held for 5 min before being rapidly quenched to room temperature to form the amorphous form. To prepare crystalline Form III, the amorphous sample is first annealed at 50-60° C. for 4-5 days, then transferred to a 100° C. oven and monitored by polarized light microscopy periodically until enough Form III appears and crystallizes completely on the cover glass.

Figure 2C:
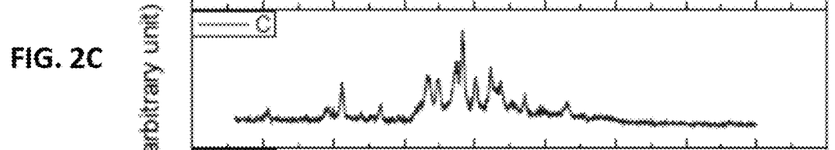
(FIG. 2C) Form III.
Figure 2D:
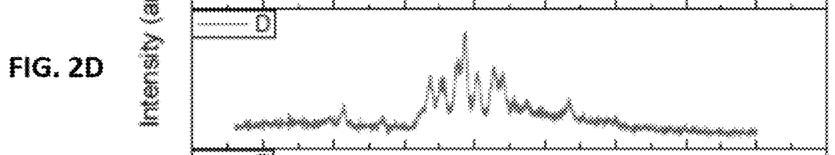
(FIG. 2D) Form III powder annealed at 100° C. for 10 h.
Figures 2E, 2F:
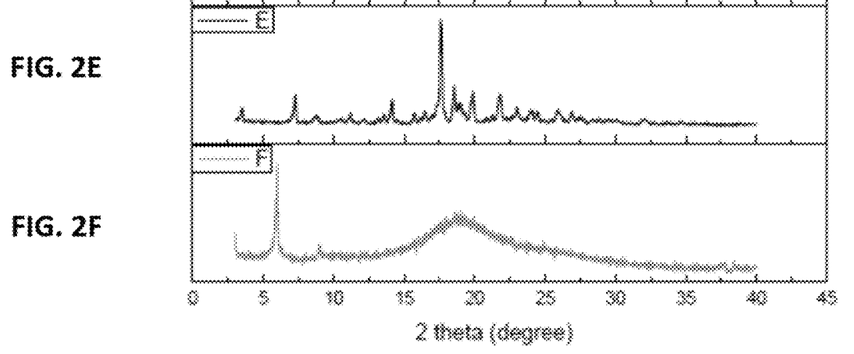
(FIG. 2E) Form III powder annealed at 120° C. for 10 h.
(FIG. 2F) Amorphous ITZ prepared by rapid melt quenching.

As shown in FIG. 1, amorphous ITZ recrystallized from melt between two glass coverslips into three distinct growth zones with different morphologies under different conditions. FIGS. 2A, 2B and 2C show the XRPD patterns for the three different growth zones, respectively. The diffraction pattern of the first zone was consistent with that of the commercial Form I, while the second one exhibited the same diffraction pattern as that of Form II, as first documented in the U.S. Application Publication No. 2003/0100568, also U.S. Pat. No. 7,193,084 (each of which is incorporated herein in its entirety). The third zone, termed Form III, was characterized by signature peaks at approximately 11.9°, 16.7°, 17.4°, 18.7°, 19.1°, 20.0°, and 21.1°, indicative of a new crystal form, which has not been reported previously. As with other drug materials such as felodipine 15 and nifedipine, ITZ exhibited temperature-dependent recrystallization behaviors. The morphologies of Form I and II were similar and almost indistinguishable. Form III only existed in the bulk of recrystallized ITZ (FIG. 1C). All of the three forms grew as spherulites at temperatures below 110° C. (FIG. 1D). At temperatures above 110° C., Forms I and II grew as separate faceted crystals (FIGS. 1E and 1F), whereas Form III transformed to Form II. The latter was further substantiated by annealing Form III at 100° C. and 120° C. As verified by XRPD (FIGS. 2D and 2E), annealing of Form III at 120° C. for 10 hours led to its conversion to Form II while similar treatment at 100° C. afforded no such phase transition. Form III was found to be stable at ambient conditions since scraping of the sample from the glass coverslip for XPRD analysis did not induce any solid-solid transition.

Figure 3A:
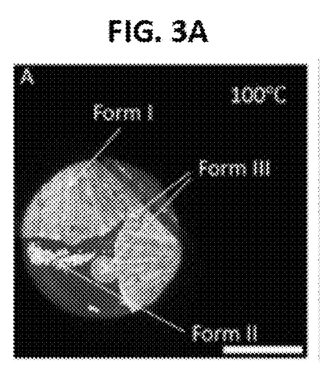
(FIG. 3A) ITZ crystals at 100° C.; arrows indicate different forms of ITZ.
Figure 3B:
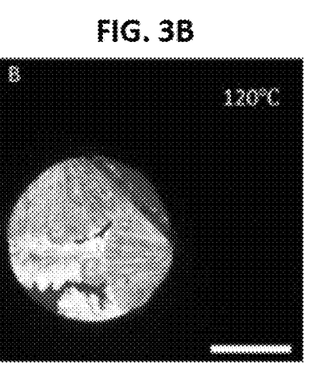
(FIG. 3B) ITZ crystals at 120° C.
Figure 3C:
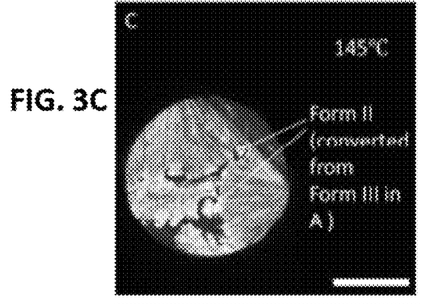
(FIG. 3C) ITZ crystals at 145° C.; Form II converted from Form III in (FIG. 3A).
Figure 3D:
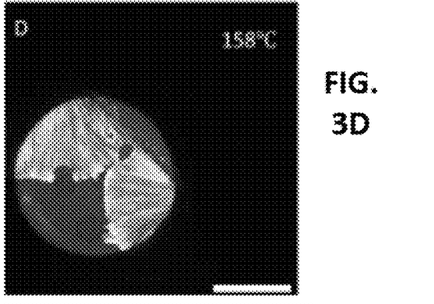
(FIG. 3D) ITZ crystals (Form I) at 158° C.
Figure 3E:
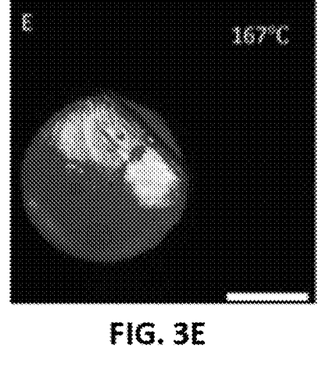
(FIG. 3E) Melting of Form I at 167° C.
Figure 3F:
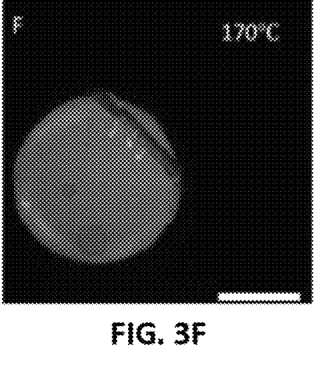
(FIG. 3F) Complete melting of Form I at 170° C. Heating rate of hot stage is 3° C./min. Scale bar equals 2000 am.
Figure 4A:
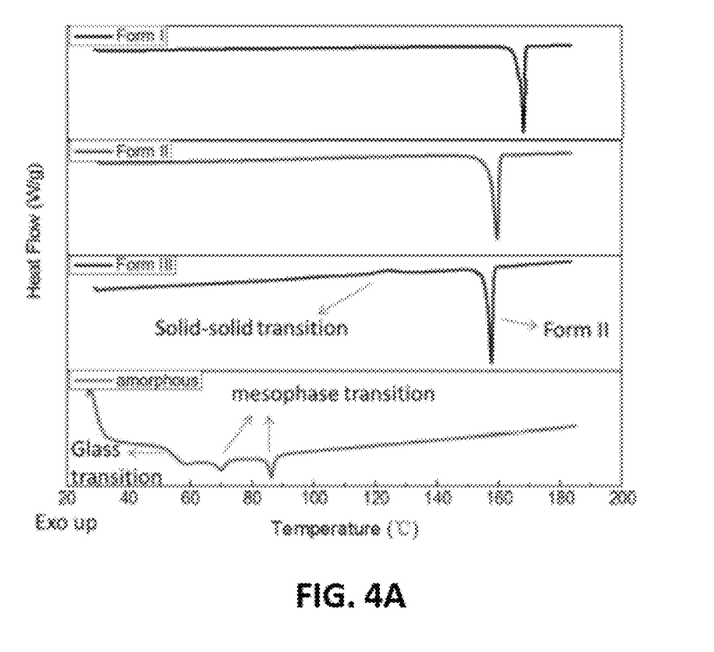
FIG. 4A shows DSC analysis of different polymorphs and amorphous form of ITZ at 3° C./min. Form I and Form II show single melting endotherms. Form III shows split peaks indicative of partial conversion to Form II during heating; the small exothermic peak at around 120° C. indicates transition of Form III to Form II. Amorphous form of ITZ was prepared by quenching of ITZ melt through rapid cooling to room temperature in a DSC pan.
Figure 4B:
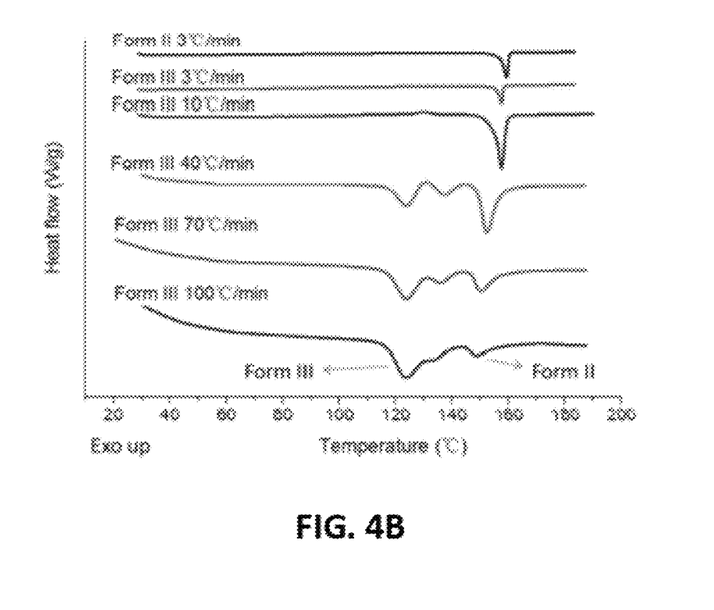
FIG. 4B shows DSC analysis of Form III samples at different heating rates. The melting endotherm of Form III began to emerge at higher heating rates.
Figure 4C:
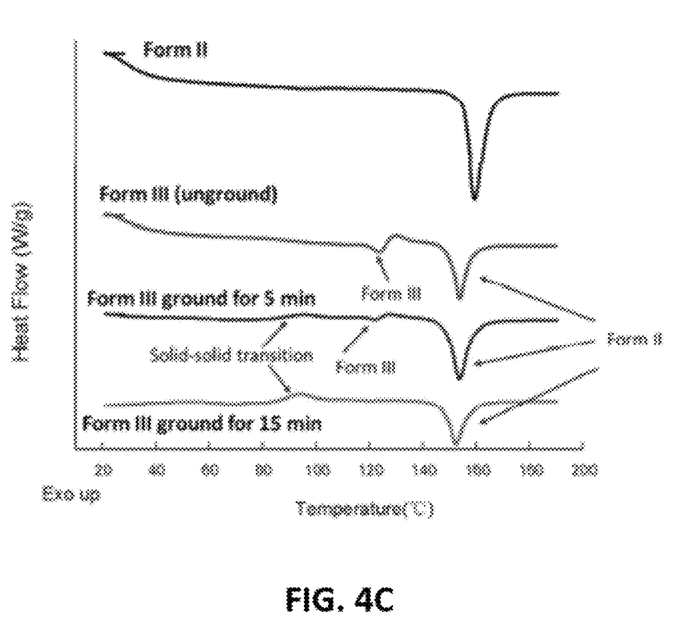
FIG. 4C shows DSC analysis of Form III samples ground for different time periods at 40° C./min; the exothermic peak at ~90° C. indicates solid phase transition from Form III to Form II.

Samples of ITZ polymorphs recrystallized from melt on glass coverslips were first examined by HSM. As shown in FIG. 3, upon heating above 100° C., Form III underwent transformation to Form II, which was completed at 145° C. (FIGS. 3B and 3C). Further heating led to melting of Form II at 158° C. (FIG. 3D), and eventually melting of Form I at around 167° C. (FIG. 3E). To gain further insight into the thermal behaviors and melting properties of the different polymorphs, DSC analyses were conducted and the respective thermograms are presented in FIG. 4A. Form I melted at 165.1° C., which is in excellent agreement with the melting point of the commercial ITZ form (Form I). The melting point of Form II (155.7° C.) is the same as that described previously. The measured molar enthalpy of fusion, $\Delta H^f$, of Form II was 60.6±1.7 kJ/mol, which is less than that ($\Delta H^f = 68.6 \pm 1.5$ kJ/mol) of Form I. The molar entropy of fusion, $\Delta S^f$, of Form II (141±4 J/mol·K) was also less than that of Form I ($\Delta S^f = 156 \pm 4$ J/mol·K). A well-defined melting endotherm and reliable $\Delta H^f$ estimate could not be obtained for Form III because it rapidly converted to Form II upon heating, as evidenced by the progressive phase changes of Form III observed with increasing heating rate in DSC (FIG. 4B). At low scanning rate, e.g., 10° C./min, a small exothermic peak appeared at ~120° C. (which possibly reflects the transition of Form III to Form II), followed by an endotherm at ~156° C., corresponding to the melting of Form II. At higher heating rates, e.g., 40° C./min, the melting endotherm of Form III started to emerge at 119.4° C., followed by a relatively small endotherm at a higher temperature, which can be attributed to the melting of recrystallized Form II from the Form III melt. Due to the co-existence of Form III and/or its melt, this Form II was seen to melt at a lower temperature than its phase pure counterpart (m.p. ~156° C.). Such a transition to Form II through the molten state appeared to occur extremely rapidly since the Form II endotherm was still discernable at the highest scanning speed (100° C./min). Consequently, in order for the melting event of Form III to become visible, the melting of Form III needs to occur faster than the concurrent recrystallization of Form II from the Form III melt, which would only be possible at sufficiently high heating rates, as substantiated by the current DSC results. However, the possibility of a transition of Form III to Form II in the solid state rather than via the molten state cannot be entirely ruled out. To verify such a possibility, Form III was subjected to grinding using a pestle and mortar for different time periods prior to DSC analysis at 40° C./min. Grinding is known to be effective for facilitating polymorphic conversion in the solid state by weakening the intermolecular bonding in the material and lowering the activation energy barrier against the conversion. As shown in FIG. 4C, no melting endotherm of Form III was observable for the ground sample; the thermogram only displayed an exothermic transition at ~90° C., and the typical melting endotherm of pure Form II at ~156° C. The exothermic event is probably a result of the solid phase transition of Form III to Form II since the Form III material remained unchanged in crystal structure after grinding, as confirmed by XRPD.

Figure 5:
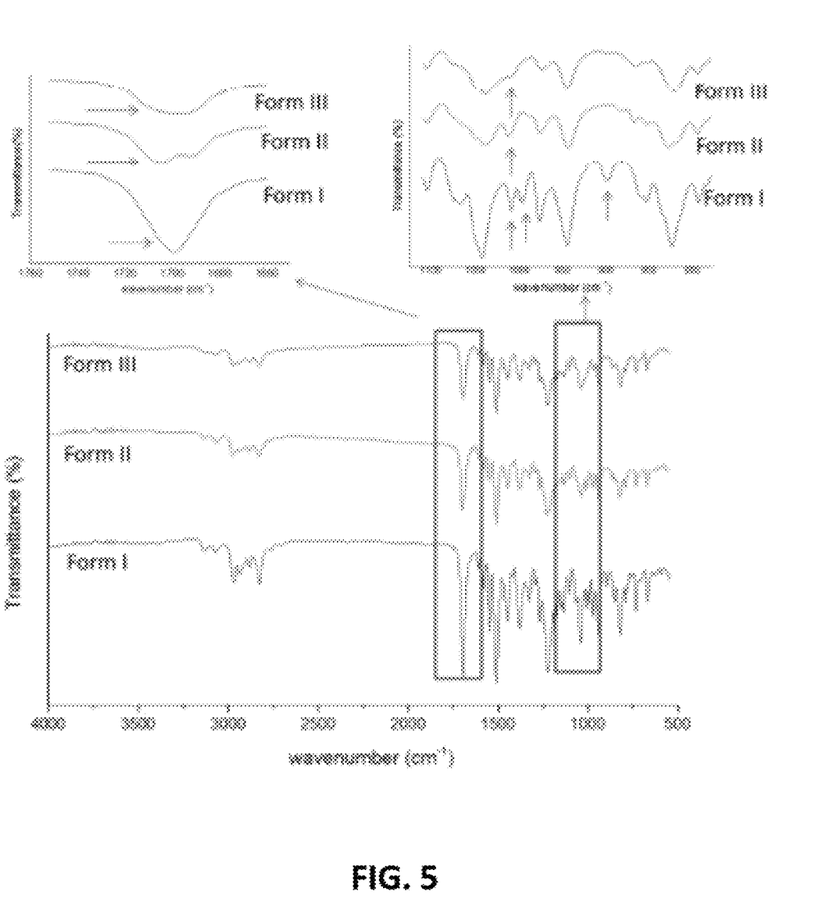

The three ITZ polymorphs also displayed distinct differences in two defined fingerprint regions of the FTIR spectra, viz. 1650 cm$^{-1}$-1750 cm$^{-1}$ and 800 cm$^{-1}$-100 cm$^{-1}$ (FIG. 5). In the first region, Form I showed a strong absorption peak at 1699 cm$^{-1}$, ascribable to the C=O stretch, while the corresponding peak of Form III occurred at 1696 cm$^{-1}$. As for Form II, peak splitting appeared at 1692 cm$^{-1}$ and 1705 cm$^{-1}$. In the second fingerprint region, Form I showed two strong absorption peaks at 998 cm$^{-1}$ and 899 cm$^{-1}$, which were absent in both Forms II and III. In addition, both Forms I and II exhibited an absorption peak at 1010 cm$^{-1}$ whose intensity decreased markedly in Form III. All these IR spectral differences provide a useful means of differentiating the various ITZ polymorphs.

Example 2. Solubility Determination

Solubilities of different polymorphs were determined by adding excess drug to 10 ml of 50% v/v aqueous ethanol in glass vials, followed by equilibration with occasional shaking at different temperatures (4° C., 10° C., 20° C., 25° C., 34° C., 40° C.) in a temperature-controlled incubator (Lovibond TC 135S, Tintometer GmbH, Dortmund, Germany) for 3 days (i.e., until equilibrium was reached). The solution was then filtered and the drug content was analyzed by UPLC (Agilent 1200 Infinity LC systems) using a UHPLC ZORBAX Eclipse Plus C18 column (2.1 mm×50 mm; 1.8 m). The mobile phase consisted of acetonitrile and 0.1% formic acid (60:40 v/v) eluted at 1 ml/min. Quantification was based on the peak area measurement by UV absorption at $\lambda=260$ nm. After the study, the residual solid in each glass vial was analyzed by DSC and XRPD to check for possible polymorphic transitions during the study. Solubility data were expressed in mole fraction as follows:

$$x_2 = \frac{n_2}{n_1 + n_2}$$

where $n_1$ is the number of moles of solvent, and $n_2$ is the number of moles of solute.

Figure 6A:
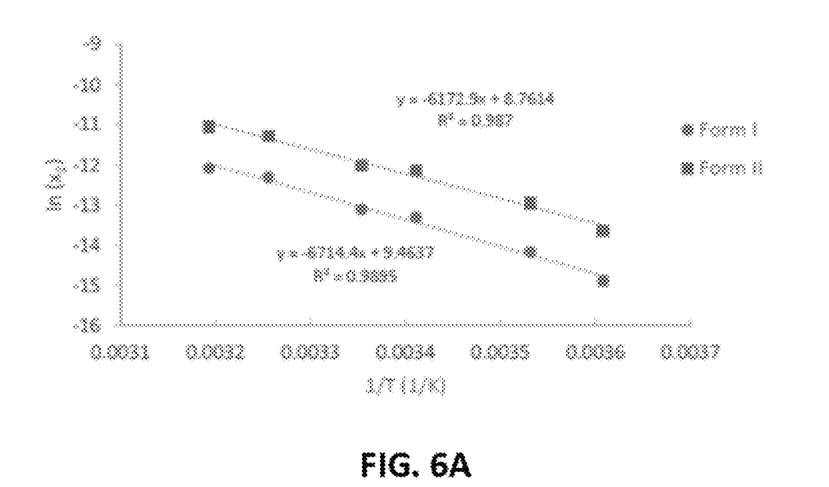
FIG. 6A shows van't Hoff plots of log solubility for ITZ Forms I and II and FIG. 6B log solubility ratio of Form II and Form I in 50% v/v aqueous ethanol. Each data point is the mean of three independent determinations.
Figure 6B:
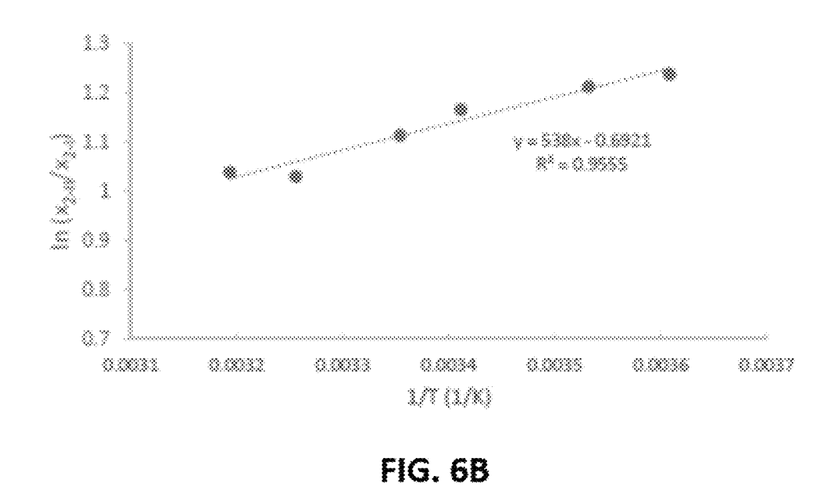

In addition to the enthalpy of fusion, equilibrium solubility and the related enthalpy of solution in a given solvent system can offer useful information on the bonding strength within the crystal lattice of a particular polymorph. FIG. 6 shows the van't Hoff solubility plot of natural logarithms of mole fraction solubility (ln $x_2$) versus the reciprocals of absolute temperature (1/T) for Form I and Form II in 50% v/v aqueous ethanol at different temperatures. According to the van't Hoff equation, the plot should be linear if the enthalpy of solution term in the equation is truly temperature-independent. 20 The molar enthalpies of solution determined for Form I and Form II from linear regression of the solubility curves in FIG. 6A were 55.8 (±2.8) kJ/mol and 51.3 (±2.9) kJ/mol respectively. The extrapolation of two linear plots yielded a transition temperature, $T_r$, of 497.8° C. at the intersection point for the two polymorphs. The enthalpy, $\Delta H_{II \to I}$, and entropy, $\Delta S_{II \to I}$, of polymorphic transition from Form II to Form I were estimated to be −4470.8 J/mol and −5.7 J/mol·K from the slope of the log solubility ratio plot in FIG. 6B and from the relation, $\Delta S_{II \to I} = \Delta H_{II \to I}/T_r$ (i.e., when $\Delta G_{II \to I}=0$), respectively. The free energies of polymorphic transition, $\Delta G_{II \to I}$, from Form II to Form I at 25° C. and 37° C., as defined by the equation, $\Delta G_{II \to I} = \Delta H_{II \to I} - T\Delta S_{II \to I}$, were calculated to be −2771 J/mol and −2703 J/mol, respectively. The solubility of Form II was about 2-3 fold higher than that of Form I in the temperature range studied. Unlike Form I and Form II which remained stable throughout the solubility study, Form III underwent conversion to Form I, as verified by DSC and XRPD analyses of the excess solid left after the study, and therefore, its saturation solubility could not be determined.

Figure 7:
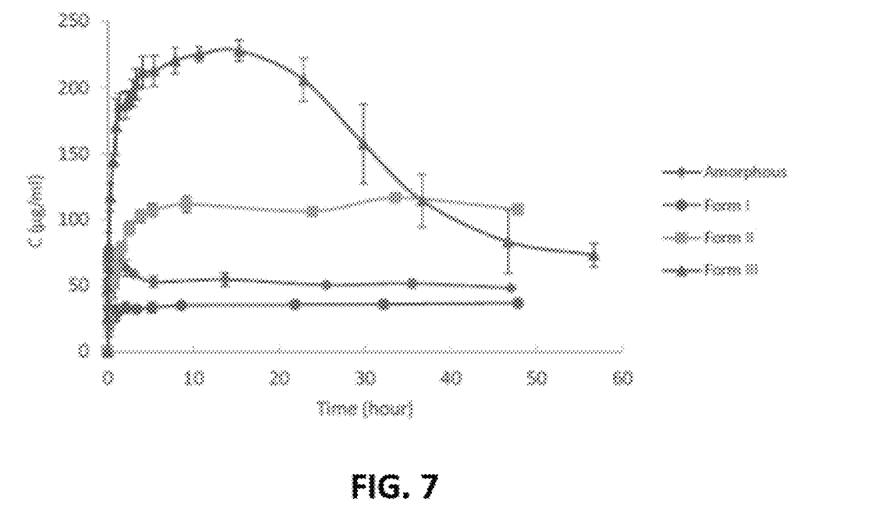
FIG. 7 shows dissolution-time profiles of ITZ Forms I, II, III and amorphous form in 50% v/v aqueous ethanol at 25° C. Form I and Form II maintained their original crystal structures while Form III and the amorphous material converted to Form I after the 3-day dissolution study. Each data point is the mean of three independent determinations
Figure 8:
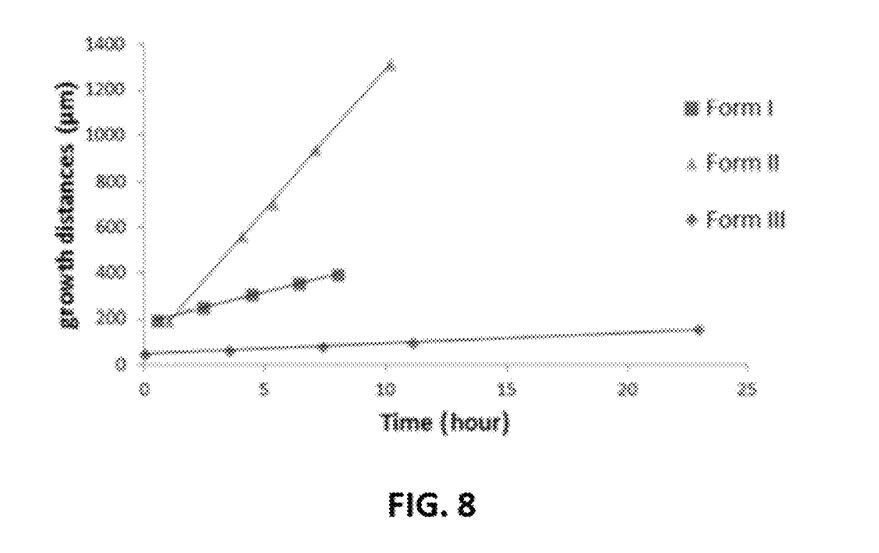
FIG. 8 shows growth distances of different ITZ polymorphs plotted as a function of time at 100° C. The data were analyzed by linear regression and the slope was taken as the crystal growth rate, u. Each data point is the mean of at least four separate measurements.
Figure 9:
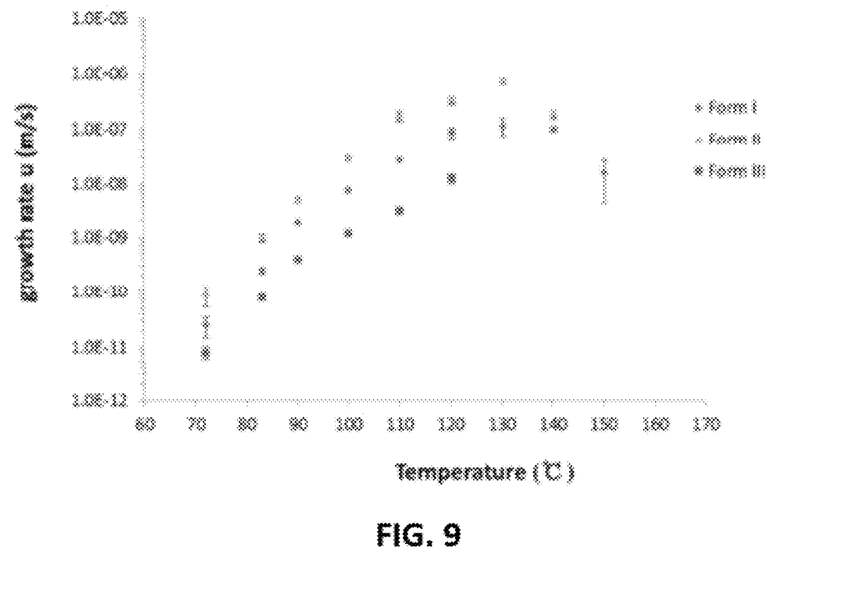
FIG. 9 shows crystal growth kinetics of different ITZ polymorphs in the melt bulk as a function of temperature. Each data point is the mean of at least four separate measurements.
Figure 10:
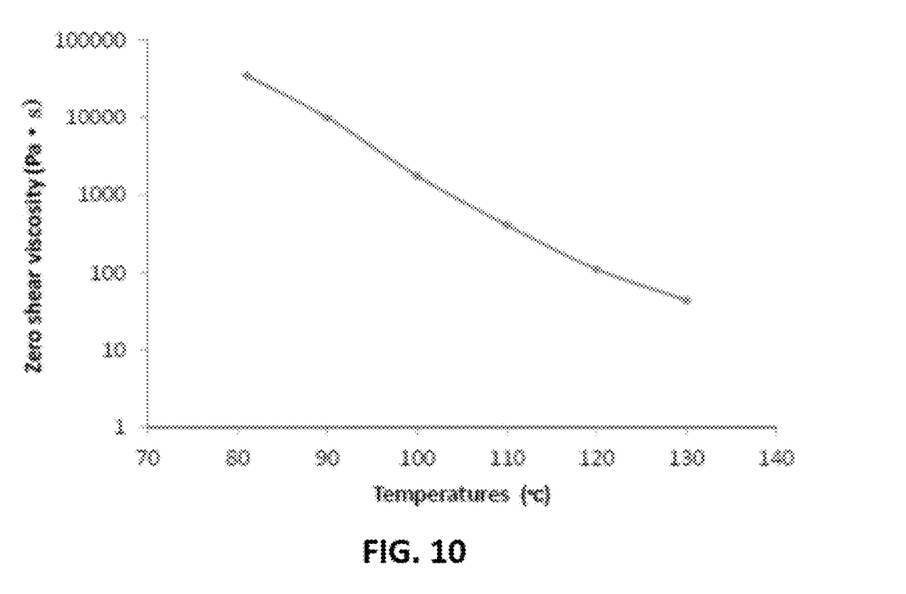
FIG. 10 shows zero-shear rate viscosities of pure ITZ in supercooled amorphous state at various temperatures.
Figure 11:
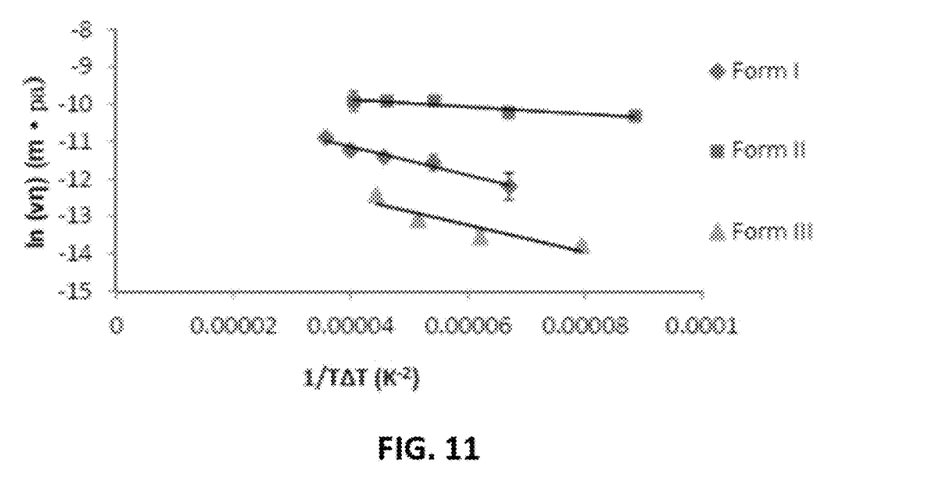
FIG. 11 shows the plot of ln(vη) versus 1/TΔT for different ITZ polymorphs. The straight lines were obtained by linear regression of the data.
Figure 12:
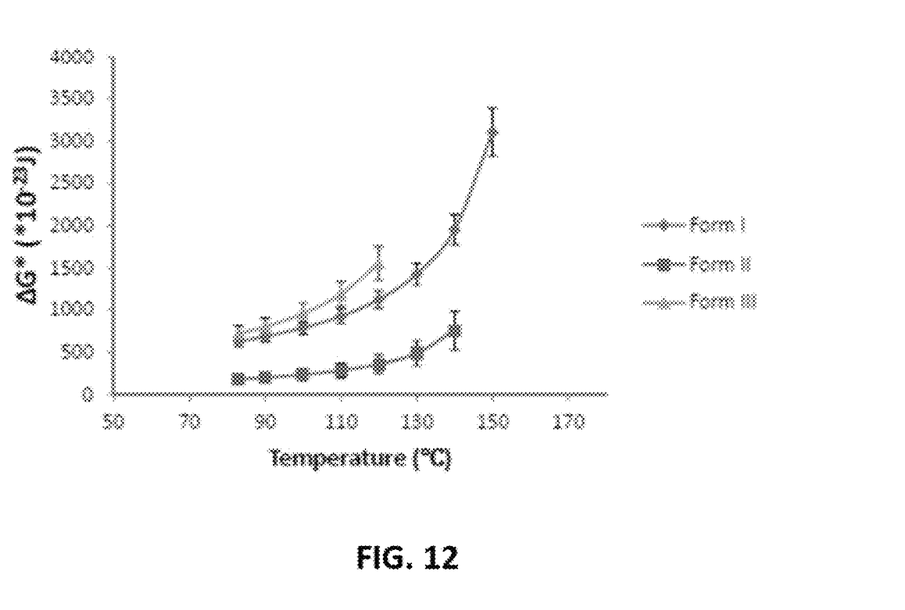
FIG. 12 shows the relationship between the activation energies, ΔG*, of crystal growth of different ITZ polymorphs and temperature.

As an alternative means to compare the solubilities of the three ITZ polymorphs, the dissolution-time profiles of these crystal forms were determined in the same solvent system. According to the Noyes Whitney equation, the dissolution rate per unit surface area of a drug solid in contact with the dissolution medium is directly proportional to its solubility under sink conditions at a constant temperature. Thus the amount of drug dissolved initially over a defined time period can provide an indirect measure of the drug solubility. FIG. 7 shows the dissolution-time profiles of the different ITZ forms in 50% v/v aqueous ethanol at 25° C. The concentrations of Form I and Form II in dissolution media increased gradually with time and plateaued off after ~10 h. The maximum drug concentration attained was 2-3 fold higher for Form II than for Form I, consistent with the equilibrium solubility data. In contrast, Form III dissolved much more rapidly than the other two forms during the initial time period, reaching a peak drug concentration about 7 fold than that of Form I at ~15 h before the drug concentration started to decline. In comparison with all three polymorphs, the dissolved drug concentration with the amorphous form increased most rapidly with time during the initial 10-min time period, but quickly dropped thereafter to an essentially constant level, equivalent to the equilibrium solubility of Form I after 50 h. DSC and XRPD analyses of all undissolved solids at the end of the dissolution studies revealed that both Form III and the amorphous form were converted to Form I in the dissolution media while Form I and Form II remained unchanged in their crystal structures.

Example 3. Determination of Crystal Growth Rates of ITZ Polymorphs

Due to the extremely slow crystal growth rates of ITZ polymorphs at room temperature, all growth rate measurements were conducted at elevated temperatures (i.e., 70° C.-140° C.). Measurements at temperatures above 100° C. were performed by hot stage microscopy (HSM); samples were placed on a Linkam THMS 600 hot stage, and growth rate was measured in real time. For the studies conducted at 70° C.-100° C., samples were maintained at a constant temperature in a temperature-controlled oven in the presence of $P_2O_5$ (~0% RH), and removed at predetermined time points for growth rate measurement under the polarized light microscope. Crystal growth rate at a defined temperature was measured from the advancing speed of crystal front into the melt. A plot of crystal size versus time was found to be linear and the slope was taken as the growth rate. Each reported growth rate was the average of at least four independent measurements.

Example 4. Powder Dissolution Studies

All powder samples for dissolution testing were first sieved through an 80 mesh-screen (180 μm), and only particles with sizes smaller than 180 m were used. An accurately weighed amount (20±0.2 mg) of each ITZ polymorph or ITZ amorphous powder (made by rapid melt quenching) was dispersed in 25 ml 50% v/v aqueous ethanol with continuous stirring at 100 rpm in a round bottom flask, equilibrated inside a temperature-controlled incubator (Lovibond TC 135S, Tintometer GmbH, Dortmund, Germany) at 25° C. At appropriate time intervals, a 400 μl aliquot of each solution was withdrawn, filtered through 0.22 m membrane filters, and diluted with a suitable amount of 50% v/v aqueous ethanol prior to UPLC analysis. Each sample withdrawn was replaced by the same volume of fresh dissolution medium. The method of drug content detection was the same as described in the preceding section. At the end of the dissolution study, the undissolved solid left in the medium was checked by DSC or XRPD for possible polymorphic transition.

Example 5. Viscosity Measurement

The steady shear viscosities of amorphous ITZ at different temperatures were measured using an ARES rheometer (TA instruments, Hong Kong). The method was essentially the same as that reported previously. Briefly, measurements were conducted using two 25 mm-diameter parallel plates with a 0.8-mm gap size between them. Nitrogen gas was used to control the temperature inside the heating hood. ITZ crystalline powder was melted between the two parallel plates and the sample was held isothermally at a temperature 5° C. higher than the melting point of ITZ for a few minutes to ensure complete melting. Afterwards, the temperature was lowered to a predefined temperature, and the upper plate was then lowered and the excess material was trimmed off along the border of the plate. The sample was equilibrated at the test temperature for 15 min and then a shear deformation was applied at a rate of 0.1 $s^{-1}$ to 10 $s^{-1}$ at a constant temperature. The shear viscosity value was recorded when the shear rate reading became steady.

Although the foregoing invention has been described in some detail by way of illustration and example for purposes of clarity of understanding, one of skill in the art will appreciate that certain changes and modifications may be practiced within the scope of the appended claims. In addition, each reference, including all of the U.S. patents, U.S. patent application publications, U.S. patent applications, foreign patents, foreign patent applications and non-patent publications referred to in this specification are incorporated herein by reference, in their entirety, to the extent not inconsistent with the present description. Where a conflict exists between the instant application and a reference provided herein, the instant application shall dominate.

What is claimed is:

1. A crystalline form of itraconazole characterized by an X-ray powder diffraction (XRPD) pattern comprising three or more peaks at 11.9, 16.7, 17.4, 18.7, 19.1, 20.0 and 21.1 degrees 2θ (±0.2 degrees 2θ), wherein the XRPD is made using $CuK_{\alpha 1}$ radiation.

2. The crystalline form of claim 1, characterized by an X-ray powder diffraction (XRPD) pattern comprising five or more peaks at 11.9, 16.7, 17.4, 18.7, 19.1, 20.0 and 21.1 degrees 2θ (±0.2 degrees 2θ), wherein the XRPD is made using $CuK_{\alpha 1}$ radiation.

3. The crystalline form of claim 1, characterized by an XRPD pattern comprising peaks at 11.9, 16.7, 17.4, 18.7, 19.1, 20.0 and 21.1 degrees 2θ (±0.2 degrees 2θ), wherein the XRPD is made using $CuK_{\alpha 1}$ radiation.

4. The crystalline form of claim 1, characterized by the XRPD pattern substantially in accordance with that of FIG. 2C.

5. The crystalline form of claim 1, characterized by a Fourier Transform Infrared (FTIR) spectrum comprising a peak at 1696 $cm^{-1}$.

6. The crystalline form of claim 1, characterized by a melting point temperature of 119° C.

7. The crystalline form of claim 1, characterized by
   an XRPD pattern comprising peaks at 11.9, 16.7, 17.4, 18.7, 19.1, 20.0 and 21.1 degrees 2θ (±0.2 degrees 2θ), wherein the XRPD is made using $CuK_{\alpha 1}$ radiation; and
   FTIR spectrum comprising a peak at 1696 $cm^{-1}$.

8. The crystalline form of claim 1, characterized by
   an XRPD pattern comprising peaks at 11.9, 16.7, 17.4, 18.7, 19.1, 20.0 and 21.1 degrees 2θ (±0.2 degrees 2θ), wherein the XRPD is made using $CuK_{\alpha 1}$ radiation;
   FTIR spectrum comprising a peak at 1696 $cm^{-1}$; and
   a melting point temperature of 119° C.

9. The crystalline form of claim 1, substantially free of itraconazole crystalline Form I and Form II.

10. A method of preparing a crystalline Form III of itraconazole, comprising:
    heating solid amorphous itraconazole at a temperature of from about 30° C. to about 100° C., thereby preparing crystalline Form III of itraconazole.

11. The method of claim 10, wherein the crystalline Form III of itraconazole is the crystalline Form III of claim 1.

12. A pharmaceutical composition comprising a therapeutically effective amount of a crystalline form of itraconazole of, claim 1 and a pharmaceutically acceptable carrier or excipient.

* * * * *